(12) United States Patent
Tisdell et al.

(10) Patent No.: US 6,265,424 B1
(45) Date of Patent: Jul. 24, 2001

(54) 3-(SUBSTITUTED PHENYL)-5-THIENYL-1,2, 4-TRIAZOLE COMPOUNDS WITH ACTIVITY AGAINST WHITEFLY

(75) Inventors: Francis E. Tisdell, Carmel; James T. Pechacek, Indianapolis; Vidyadhar B. Hegde, Carmel; Joe R. Schoonover, Jr., Brownsburg; Leonard P. Dintenfass, Indianapolis; James M. Gifford, Lebanon; Maurice C. Yap, Zionsville; Donald H. DeVries, Fishers, all of IN (US); Christopher T. Hamilton, Midland, MI (US); Norman R. Pearson, Carmel; Mary L. Ash, Zionsville, both of IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/426,078

(22) Filed: Oct. 22, 1999

Related U.S. Application Data

(60) Provisional application No. 60/105,466, filed on Oct. 23, 1998.

(51) Int. Cl.$^7$ ........................ A01N 43/653; C07D 409/04
(52) U.S. Cl. ........................................ 514/383; 548/266.2
(58) Field of Search ........................ 514/383; 548/266.2

(56) References Cited

U.S. PATENT DOCUMENTS

| 4,018,793 | 4/1977 | Stoss et al. ........................ 260/330.5 |
| 6,015,826 | 1/2000 | Pechacek et al. ..................... 514/383 |

FOREIGN PATENT DOCUMENTS

| 559363 | 9/1993 | (EP) . |
| 572142 | 12/1993 | (EP) . |
| 648752 | 4/1995 | (EP) . |

*Primary Examiner*—Patricia L. Morris
(74) *Attorney, Agent, or Firm*—Craig E. Mixan; Donald R. Stuart

(57) ABSTRACT

3-(Substituted phenyl)-5-(thienyl)-1,2,4-triazole compounds are useful as insecticides and acaricides.

10 Claims, No Drawings

3-(SUBSTITUTED PHENYL)-5-THIENYL-1,2,4-TRIAZOLE COMPOUNDS WITH ACTIVITY AGAINST WHITEFLY

RELATED APPLICATION

This application claims priority from United States Provisional Patent Application Ser. No. 60/105,466, filed Oct. 23, 1998.

FIELD OF THE INVENTION

This invention provides new compounds that are useful as insecticides and acaricides, and methods of controlling insects and mites using the compounds. The compounds are of particular interest for their activity against whitefly.

BACKGROUND OF THE INVENTION

There is an acute need for new insecticides and acaricides. Insects and mites are developing resistance to the insecticides and acaricides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides and acaricides. Therefore a need exists for new insecticides and acaricides, and particularly for compounds that have new or atypical modes of action.

US patent application Ser. No. 09/048,601, filed Mar. 26, 1998, dicloses a genus of insecticidal 3-(substituted phenyl)-5-thienyl-1,2,4-triazoles. The disclosed compounds are primarily active against mites and aphids. It has now been discovered that a particular subclass of the genus disclosed in the '601 application have greatly improved activity against other insects, such as whitefly.

SUMMARY OF THE INVENTION

This invention provides novel substituted thienyl triazole derivatives especially useful for the control of insects and mites.

More specifically, the invention provides novel insecticidally active compounds of the formula (1)

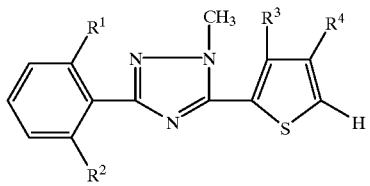

wherein
R$^1$ and R$^2$ are independently F or Cl; and
a) R$^3$ is CH$_3$ and R$^4$ is Cl or Br, or
b) R$^3$ and R$^4$ are both Br.

DETAILED DESCRIPTION

Synthesis

Compounds of formula (1) can be prepared by the methods described in U.S. Pat. Nos. 5,380,944 and 5,284,860 (Production Methods 1, 2 and 3).

A process for preparing compounds of formula (1) is illustrated in the following Scheme I:

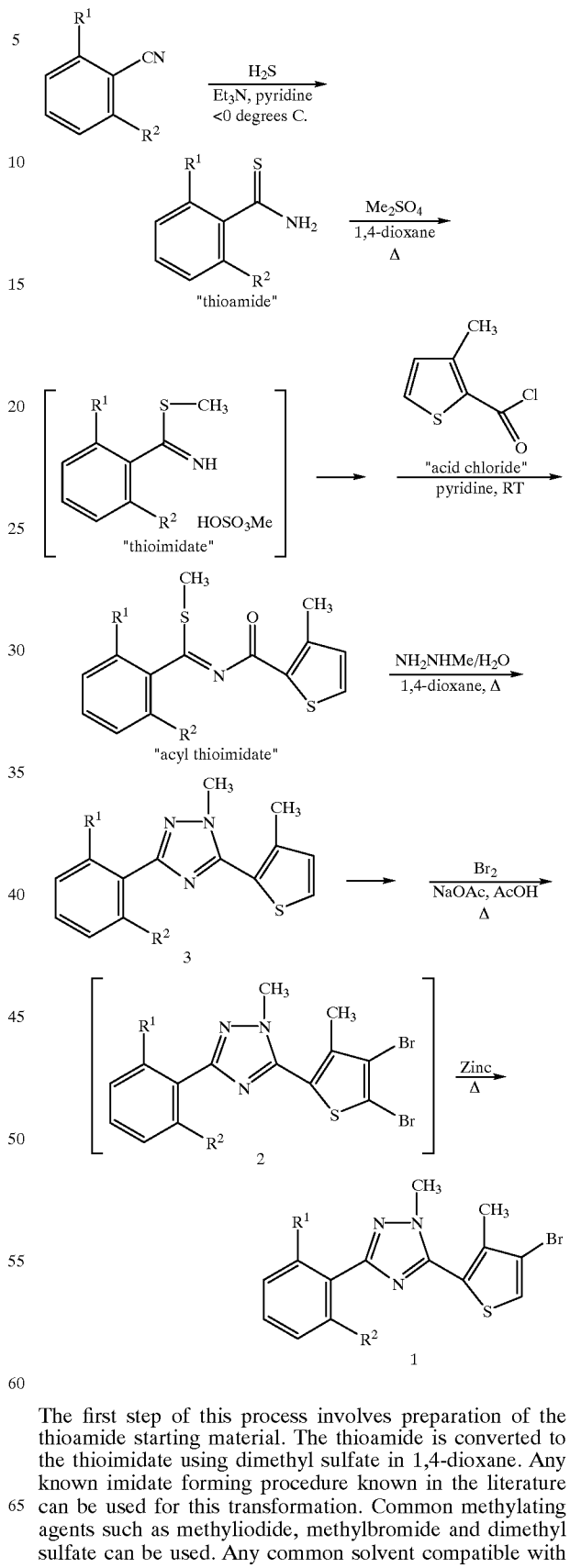

The first step of this process involves preparation of the thioamide starting material. The thioamide is converted to the thioimidate using dimethyl sulfate in 1,4-dioxane. Any known imidate forming procedure known in the literature can be used for this transformation. Common methylating agents such as methyliodide, methylbromide and dimethyl sulfate can be used. Any common solvent compatible with the reaction conditions can be used, with toluene, acetonitrile, 1,4-dioxane, THF, and 1,2-dichloroethane most convenient. Reaction temperatures range from RT to the reflux temperature of the solvent. The thioimidate can be isolated as its salt or used directly without isolation in the next transformation.

The thioimidate is next acylated with 3-methyl-2-thiophenecarbonyl chloride ("acid chloride") to give the acyl thioimidate adduct. Any known acylation conditions can be used for this transformation. Any common organic and inorganic base can be used, with $Na_2CO_3$, $NaHCO_3$, pyridine and triethylamine most convenient. Preferred solvents include 1,4-dioxane, THF, dichloromethane, and 1,2-dichloroethane, but any solvent compatible with the reaction conditions can be used. Reaction temperatures in the 0° to 60° C. range are suitable, with temperatures near RT most convenient. The acyl thioimidate is isolated by dilution of the reaction mixture with water and filtration followed by air drying. This acyl thioimidate is typically of sufficient purity to be used directly in the following cyclization step.

The acyl thioimidate is cyclized to the 1,2,4-triazole ring system by treatment with methylhydrazine. The methylhydrazine can be added neat or as a solution in a compatible solvent such as water. Any solvent compatible with the reaction conditions can be used, with toluene, 1,4-dioxane, THF, and short chain alcohols preferred. The methylhydrazine can be added all at once to the reaction mixture, or added in portions over a 1 hour time period. The cyclization can be carried out in the temperature range of RT to reflux temperature of the solvent being used. Ratios of the intermediate 3 to its off-isomer 4 range from 6:1 to 40:1 depending upon the reaction conditions used.

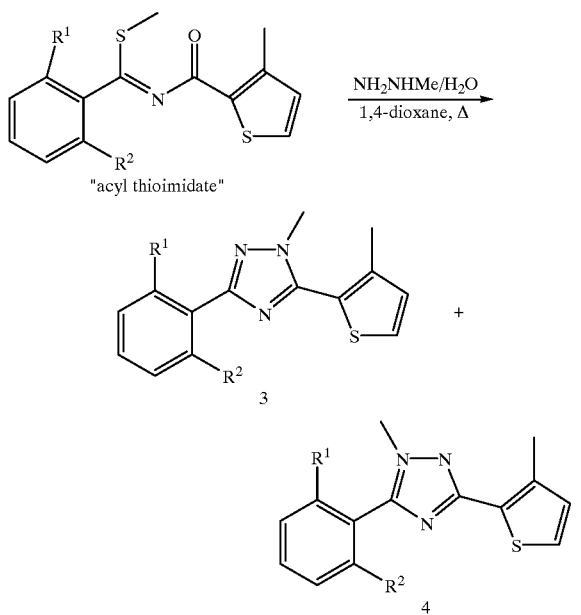

It is convenient to use 1,4-dioxane at a cyclization temperature of 80° C. to give a 30:1 ratio of isomers. Workup consists of removal of the solvent followed by crystallization from a suitable solvent such as 95% EtOH. Alternately, the reaction mixture can be diluted with water and filtered to provide the intermediate 3. Air drying provides product of sufficient purity for the next bromination step.

The last two steps illustrated in Scheme I are the bromination of triazole 3 to give the dibromo intermediate 2, followed by removal of one of the bromine atoms. Any standard brominating reagent known in the literature can be used, with $Br_2$ being the most convenient. Two to five molar equivalents of $Br_2$ can be used at temperatures from 25° to reflux temperature of the solvent. Time of reaction range from 1 hour to 24 hours. Any solvent compatible with bromination conditions can be used such as 1,4-dioxane, 1,2-dichloroethane, and acetic acid. The generated HBr can be neutralized by running the reaction in the presence of a proton acceptor such as sodium acetate. It was found most convenient to run the reaction in acetic acid with sodium acetate using four equivalents of $Br_2$.

The dibromo analogue 2 can be isolated or one may proceed directly into the next chemical transformation, if desired, without isolation. In the last step, zinc dust is added to the reaction mixture to reduce off the 5-bromine on the thiophene ring. Any known methods of aromatic halogen reduction could be used, but zinc dust was found most convenient. Two to three equivalents of zinc can be used; the extra molar equivalents were needed to reduce unreacted $Br_2$. The temperature of the reduction ranged from 25° to 90° C. This reduction is highly selective and leaves the 4-bromine of the thiophene ring unaffected. The product is conveniently isolated by dilution of the reaction mixture with water followed by filtration.

A preferred synthetic method is illustrated in the following Scheme II:

Scheme II

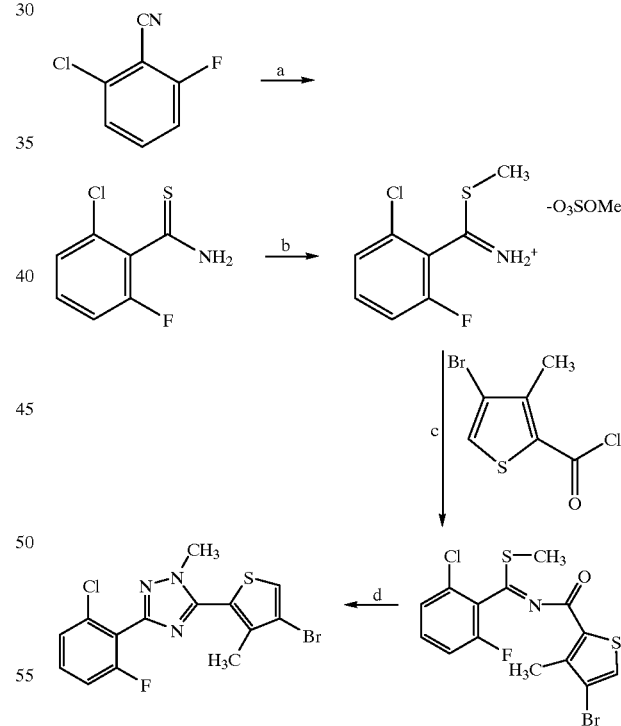

Conditions for each step in Scheme II are as follows: a) $H_2S/Et_3N$/Pyridine, −20° C., b) $(CH_3O)_2SO_2$, 1,4-dioxane, 80° C., c) pyridine, 4-bromo-TAC, 30° C., d) $MeNHNH_2/H_2O$, 1,4-Dioxane, 80° C.

The 4-bromo-3-methyl-2-thiophenecarbonyl chloride used in step c of Scheme I can be prepared using the procedure illustrated in Scheme III:

Scheme III

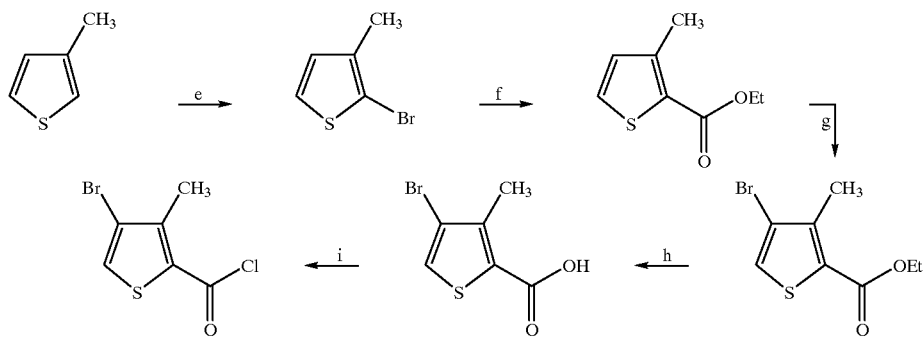

Conditions for each step in Scheme III are as follows:

e) $Br_2$/succinimide, f) 10% Pd/C, DPPP, 0.2 mol %, CO pressure, EtOH, NaOAc, g) i) 2 $Br_2$/2 NaOAc/HOAc, 80° C., ii) Zn dust, $HOAc/H_2O$, h) $NaOH/H_2O$, i) $SOCl_2$/DMF, 1,2-DCE.

Scheme III illustrates use of ethyl 3-methyl-2-thiophenecarboxylate as the intermediate utilized in step g, but any short chain alkylester of 3-methyl-2-thiophenecarboxylic acid may be used. These include, but are not limited to, methyl, ethyl, propyl or butyl. Most convenient are methyl or ethyl esters of 3-methyl-2-thiophenecarboxylic acid.

Methyl 3-methyl-2-thiophenecarboxylate may be prepared by a Grignard reaction of 2-bromo-3-methylthiophene with dimethylcarbonate. Either the methyl or ethyl ester of 3-methyl-2-thiophene carboxylic acid may be prepared by Fisher esterification with the appropriate alcohol, or by reaction of 3-methyl-2-thiophenecarboxylic acid chloride with the appropriate alcohol.

Yet another process for preparing compounds of formula (1) is illustrated in Scheme IV:

Scheme IV

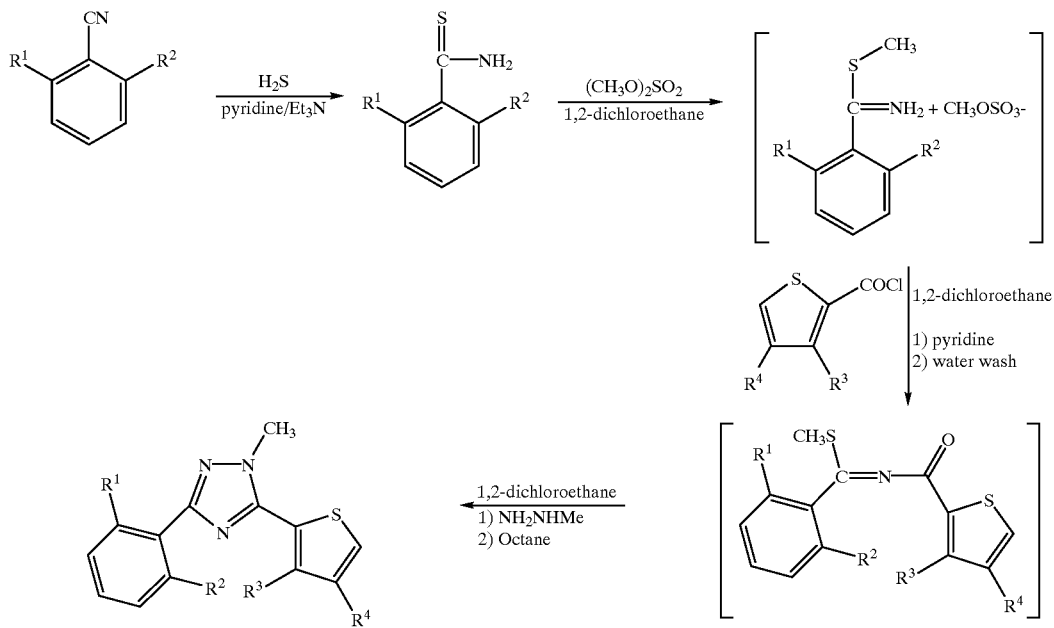

Yet another process for preparing compounds of formula (1) is illustrated in the following reaction Scheme V:

Scheme V

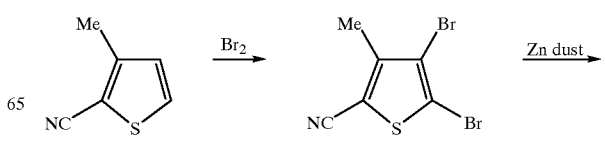

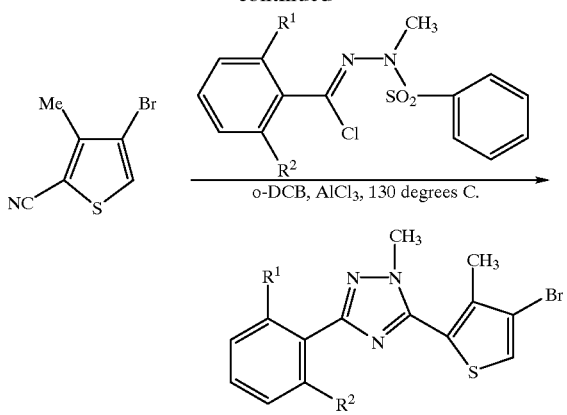

The N-((methyl)benzenesulfonylamino)-(2-fluoro-6-chlorophenyl)chloroimine used in the final step is prepared as disclosed in U.S. Pat. No. 5,380,944. In one of its aspects, therefore, the invention provides a process for preparing 3-(2-chloro-6-fluorophenyl)-1-methyl-5-(4-bromo-3-methyl-2-thienyl)-1H-1,2,4-triazole which comprises:
 a) reacting 4,5-dibromo-2-cyano-3-methylthiophene with zinc dust to provide the required 4-bromo-2-cyano-3-methylthiophene starting material;
 b) reacting the 4-bromo-2-cyano-3-methylthiophene starting material with a compound of the formula

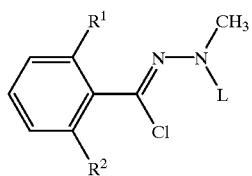

where $R^1$ and $R^2$ are as defined above and L is a conventional amino protecting group. Examples of onventional amino protecting groups include, but are not limited to, the carbobenzyloxy group, tertiary alkoxycarbonyl groups, amides, phosphinyl and phosphoryl groups, and sulfenyl and sulfonyl groups.

Additional methods of preparation are illustrated in the following examples.

EXAMPLE 1

3-(2-chloro-6-fluorophenyl)-5-(3-methyl-4-bromothien-2-yl) 1-methyl [1,2,4] triazole A. 3-(2-fluoro-6-chlorophenyl)-5-(3-methyl-2-thienyl)-1-methyl-1,2,4-triazole N-phenylsulfonyl-N-methyl-(2-fluoro-6-chloro) benzhydrazonoyl chloride (2.21 g, 6.15 mmol), aluminum chloride (0.57 g, 4.3 mmol) and 3-methyl-2-cyanothiophene (1.0 g, 8.1 mmol) were combined in 1,2-dichlorobenzene (2 ml) and heated at 130° C. for 1½ hours. Upon cooling reaction was diluted with 1 M NaOH and extracted with ether, washed with brine, and dried over $MgSO_4$. Chromatography ($SiO_2$, 25% ethyl acetate: hexane) afforded the product as a white solid (1.17 g, 62%) MP 80–82° C.; H NMR 7.45 (d, 1H) 7.35 (m, 2H) 7.15 (m, 1H) 7.00 (d, 1H)

B. 3-(2-fluoro-6-chlorophenyl)-5-(3-methyl-5-bromo-2-thienyl)-1-methyl-1,2,4-triazole 3-(2-fluoro-6-chlorophenyl)-5-(3-methyl-2-thienyl)-1-methyl-1,2,4-triazole (1.18 mmol., 364 mg) was dissolved in glacial acetic acid (4 ml). Bromine (2.36 mmol, 0.124 ml) was added in two portions and the reaction allowed to stir 5 days at room temperature. Diluted with water and extracted into diethyl ether, washed with saturated $NaHCO_3$ and brine, dried over $MgSO_4$. Concentrated to a white solid. Wgt. 0.51 g, recrystallized from hexane ethyl acetate to afford the product as a white solid (0.37 g, 81%) MP 117–118° C.; Anal. Calcd. For $C_{14}H_{10}BrClFN_3S$; C, 43.44; H, 2.60; N, 10.86. Found; C, 43.46; H, 2.71; N, 10.81.

C. 3-(2-chloro-6-fluorophenyl)-5-(3-methyl-4,5-dibromothien-2-yl) 1-methyl [1,2,4] triazole Bromine (2.7 mL) was added to a solution of 3-(2-chloro-6-fluorophenyl)-5-(3-methyl-5-bromothien-yl)1-methyl [1,2,4] triazole (10.0 g), sodium acetate (4.25 g) in acetic acid (100 mL) under a nitrogen atmosphere. This brown suspension was heated at 70° C. for 2.0 h. After cooling, diethyl ether (500 mL) was added and the reaction was made basic with saturated sodium bicarbonate. The ether layer was washed with $NaHCO_3$ (sat.), water, dried ($Na_2SO_4$), filtered and concentrated to yield 12 g of crude solid. Trituration with hexane gave 3-(2-chloro-6-fluorophenyl)-5-(3-methyl-4,5-dibromothien-2-yl) 1-methyl [1,2,4] triazoleas white solid (10 g, 83% yield). MP 137–138° C.; Anal. Calcd. For $C_{14}H_9Br_2ClFN_3S$; C, 36.12; H, 1.95; N, 9.03; S, 6.89. Found; C, 36.70; H, 2.00; N, 8.68; S, 6.78.

D. 3-(2-chloro-6-fluorophenyl)-5-(3-methyl-4-bromothien-2-yl) 1-methyl [1,2,4] triazole n-Butyl lithium (6.04 mL, 2.5 mmol) was slowly added over a 15 min period to 3-(2-chloro-6-fluorophenyl)-5-(3-methyl-4,5-dibromothien-2-yl) 1-methyl [1,2,4] triazole (7.0 g) in THF (100 mL) at −70° C. under a nitrogen atmosphere and stirred for 1.0 h. After the addition of the distilled water, the reaction was allowed to warm to 25° C. The reaction mixture was extracted with diethyl ether (3×100 mL). The combined ether extracts was washed with water, dried over anhydrous sodium sulfate, filtered and concentrated to crude solid. This was chromatographed on silica gel (EtOAc/Hexane, 1:1) to give 5.0 g (86% yield) 3-(2-chloro-6-fluorophenyl)-5-(3-methyl-4-bromothien-2-yl) 1-methyl [1,2,4] triazole as white solid. MP 111–112° C. ; Anal. Calcd. For $C_{14}H_{10}BrClFN_3S$: C, 43.49; H, 2.61; N, 10.87; S, 8.29. Found; C, 43.79; H, 2.66; N, 10.95; S, 8.28.

EXAMPLE 2

3-(2-chloro-6-fluorophenyl)-5-(3-methyl-4-chlorothien-2-yl) 1-methyl [1,2,4] triazole Cuprous chloride (2.9 g) was added to a solution of 3-(2-chloro-6-fluorophenyl)-5-(3-methyl-4,5-dibromothien-2-yl) 1-methyl [1,2,4] triazole in DMF and heated at 120° C. for 12 h under a nitrogen atmosphere. After cooling, HCl (1N) was added and extracted with ether (3×100 mL), washed with brine, dried ($Na_2SO_4$), filtered and concentrated to give 1.35 g of crude solid. This was chromatographed on silica gel (Hexane/EtOAc, 3:1, 2:1, 1:1) gave 3-(2-chloro-6-fluorophenyl)-5-(3-methyl-4-chlorothien-2-yl) 1-methyl [1,2,4] triazole as white solid (0.6 g, 55%) MP 117–118° C.; Anal. Calcd. For $C_{14}H_{10}BrClFN_3S$: C, 49.14; H, 2.95; N, 12.28; S, 9.37. Found; C, 48.86; H, 3.03; N, 12.04; S, 9.37.

EXAMPLE 3

3-(2-Chloro-6-fluorophenyl)-1-methyl-5-(3-methyl-4-bromo-2-thienyl)-1H-1,2,4-triazole The following example illustrates the process of Scheme I.

A. 2-Chloro-6-fluorobenzenecarbothioamide

2-Chloro-6-fluorobenzonitrile (1230 g, 7.91 mol) was weighed into a 22 L jacketed glass reactor (without bottom drain), along with $Et_3N$ (1.5 L, 10.76 mol) and pyridine (2.4 L, 29.67 mol) and the stirring solution was cooled to −18° C. under a blanket of $N_2$. The reactor $N_2$ purge mineral oil bubbler was vented to a carboy containing 16 L of 12% bleach solution. Hydrogen sulfide gas (407 g, 11.94 mol) was introduced below the surface of the cold reactor solution over a period of 5.5 hrs. During this time the reactor temperature rose from −18 to −4° C. The solution was stirred overnight at −7° C. (16 hrs), sampled by GC to ensure complete conversion of 2,6-CFBN, then quenched by vacuum transfer of the reactor solution into a second 22 L flask containing 14 L of cold water stirring at 300 RPM (Note: Quenching into a well-stirred tank of cold water produces small white particles of easily filtered product). After the vacuum transfer was completed, another 2 L of cold water was added to the stirring slurry. The light yellow slurry of white solid was drained from the quench tank into bottles, and the solid product was collected by filtration through a course glass buchner funnel, followed by washing of the solid product with an excess of de ionized water. The white solid was air suction dried for 3 h, air dried in a glass pan overnight, then dried in a vacuum oven at 50° C. at 0.3 mm Hg for 8 hrs to give 1004 g (67%) of dry 2-chloro-6-fluorobenzenecarbothioamide, m.p. 153–157° C.

B. Methyl 2-chloro-6 fluoro-N-[(3-methyl-2-thiophene)carbonyl]benzenecarboximidothioate To a 22 L jacketed glass reactor under a $N_2$ purge was added 6 L of 1,4-dioxane via a pump. After the mechanical stirrer had been started, 1140 g (6.0 mol) of 2-chloro-6 fluorobenzenecarbothioamide was added to the reactor, followed by 630 mL (6.65 mol) of dimethyl sulfate. The reaction mixture was heated to 80° C. for 1.5 h. During the course of heating, the reaction mixture became a solution near 55° C., with a precipitate reforming as the reaction proceeded. LC analysis indicated <2% area starting thioamide and 96% area methyl 2-chloro-6-fluorobenzenecarboximidothioate methylsulfonate salt ("thioimidate"). The reaction mixture was cooled to 30° C., and 1.2 L (15 mol) of pyridine was added. When the reaction temperature had fallen back below 30° C., 970 g (6.04 mole) of 3-methyl-2-thiophenecarbonyl chloride ("acid chloride") was added via a PE dropping funnel over 20 min. An exotherm of seven degrees was observed during this addition. After stirring at room temperature for 1 h, LC analysis indicated <3% area of the thioimidate and 93% area acyl thioimidate. To the reaction mixture was added 9 L of water, and the mixture stirred at room temperature for 1 h. The mixture was filtered through a crock filter with vacuum removal of the mother liquor into a second 22 L glass reactor. The white solid was air dried in a glass pan overnight to give 2000 g of a white powder, 98% LC area. This material was used directly in the next step without further purification.

C. 3-(2-Chloro-6-fluorophenyl)-1-methyl-5-(3-methyl-2-thienyl)-1H-1,2,4-triazole To a 22 L jacketed glass reactor under a $N_2$ purge was added 9 L of 1,4-dioxane via a pump. The $N_2$ purge outlet was connected to a carboy containing 12 L of fresh 12% wt bleach solution. To the stirred dioxane was added 1970 g (6 mol) of methyl 2-chloro-6 fluoro-N-[(3-methyl-2-thiophene)carbonyl]benzenecarboximido-thioate and the mixture heated to 80° C. During heating the mixture became a clear solution. Upon reaching 80° C., a solution of 400 mL (7.5 mol) of methylhydrazine in 600 mL of water was added over 20 min via a pump. The mixture was heated near 80° C. for 3.5 h, when GC area analysis indicated 2% starting acyl thioimidate, 94% desired product, and 3% off-isomer 4. The reaction mixture was cooled to 30° C. and vacuum transferred to a roto-evaporator connected to bleach trapping. The reaction mixture was concentrated to an amber oil, dissolved in 800 mL of 95% EtOH, and transferred to a 4 L Erlynmeyer flask. The solution was scratched and seeded with the title compound and allowed to crystallize in a refrigerator overnight. After filtration the precipitate was air dried in a glass pan overnight to give 1376 g of an off-white powder, 99% area GC. This material was used directly in the next step without further purification.

D. 3-(2-Chloro-6-fluorophenyl)-1-methyl-5-(3-methyl-4-bromo-2-thienyl)-1H-1,2,4-triazole The triazole 3-(2-Chloro-6-fluorophenyl)-1-methyl-5-(3-methyl-2-thienyl)-1H-1,2,4-triazole (1715 g, 5.57 mol) and anhydrous sodium acetate (1830 g, 22.3 mol) were weighed as solids into a 22 L jacketed glass reactor under a slow $N_2$ purge, followed by 8.5 L glacial AcOH. Heating of the mixture was begun, and at 66° C. a solution of $Br_2$ (1.15 L, 22.3 mol) in 2.5 L glacial AcOH was added by peristaltic pump over a period of 40 min., at a rate to keep the reaction temperature below 85° C. During heat up most of the solids dissolve. The stirring red solution was heated 1 h at 80° C. and then a sample was removed and analyzed by GC to verify >99% conversion to the dibromo intermediate. Cooling was placed on the jacket, and 1695 g ice was added to the solution, which dropped the temperature from 70° C. to 50° C. At 38° C. zinc powder (815 g, 12.5 mol) was added in 55 g shots over a period of 40 min to dispel excess $Br_2$. During this addition the reactor temperature rose to 71° C. Additional zinc powder (650 g, 9.9 mol) was then added in 50 g shots over a period of 50 min with a stream of $N_2$ passing through the reactor to dispel $H_2$ gas safely. During the addition of this second portion of zinc powder, jacket heating (85° C.) was applied to bring the reaction mixture to 78° C. (Note: zinc addition at this point leads to $H_2$ gas evolution and should be done at such a rate as to control the rate of evolution and maintain precautions against flammability and explosion hazards). After zinc addition was completed, the reactor was stirred at 78° C. for 15 min, then was sampled for GC analysis (Note: the reactor can be maintained at this point at 80° C. overnight to keep the product dissolved if insufficient time exists to carry out the filtration). The solution was filtered warm through a layer of celite on a course glass buchner funnel (pre warmed at 100° C.) to remove residual zinc particulates. The celite cake was washed with a small amount of additional glacial AcOH. The clear light yellow filtrate was diluted with cold water while stirring until the cloud point was reached and product crystallization began. Excess cold water was then added to precipitate the remainder of the solid product. Part of this dilution was done in 4 L Erlenmeyer flasks with magnetic stirring and part was done in a second 22 L reactor. Approximately eight 2 L portions of solution were filtered from the reactor, and approximately 18 L of quench water was used. The white solid product was collected on course glass buchner funnels, rinsed with additional de-ionized water, air suction dried for a few hours, then transferred to glass trays and air dried overnight. A final vacuum oven drying for 2.5 hrs at 0.3 mm Hg and 30° C. was carried out to give 2236 g of 3-(2-Chloro-6-fluorophenyl)-1-methyl-5-(3-methyl-4-bromo-2-thienyl)-1H-1,2,4-triazole as a white solid (theory= 2154 g), mp 118–120° C. A GC area % analysis indicated a purity of 98.1%.

EXAMPLE 4

1-Methyl-3-(2-fluoro-6-chlorophenyl)-5-(3-methyl-4-bromothiophen-2-yl)-1H-1,2,4-triazole This example illustrates the process of Scheme V.
A. Preparation of 4,5-Dibromo-3-methyl-2-thiophenecarbonitrile A solution of 0.300 g (2.43 mmol) of 3-methyl-2-thiophenecarbonitrile and 0.30 mL of DMF was treated at rt with 0.75 mL (14.6 mmol) of bromine and the dark mixture allowed to stir at ambient temperature. After 2 hours, 0.5 mL of DMF was added to aid stirring and the mixture was stirred for 30 additional minutes and then was poured into 15 mL of dilute, aqueous sodium bisulfite solution. After stirring for 10 minutes at rt, the white solid present was collected by filtration, washed with water and vacuum oven dried to afford 0.61 g (89%): mp 77–80° C.; $^1$H NMR (CDCl$_3$) 2.46 (s, 3H, CH$_3$); GC-MS (EI) 281 (M+).
B. Preparation of 4-Bromo-3-methyl-2-thiophenecarbonitrile A mixture of 0.400 g (1.42 mmol) of 4,5-dibromo-3-methyl-2-thiophenecarbonitrile, 0.186 g (2.85 mmol) of zinc dust, 4 mL of acetic acid and 1 mL of water was heated at 100–105° C. for 45 minutes. After cooling, the solvents were removed under reduced pressure and the residue was dissolved in 10 mL of ether and washed with water (2×5 mL) and dilute, aqueous sodium carbonate solution (1×5 mL). After drying (sodium sulfate), the ether was removed on the rotovap to afford 0.276 g (96%) of an off-white solid: mp 54–58° C.; $^1$H NMR (CDCl$_3$) 7.47 (s, 1H, ring-H) and 2.42 (s, 3H, CH$_3$); GC-MS (EI) 201/203 (M+).
C. Preparation of 1-Methyl-3-(2-fluoro-6-chlorophenyl)-5-(3-methyl-4-bromothiophen-2-yl)-1H-1,2,4-triazole A mixture of 0.059 g (0.163 mmol) of N-((methyl) benzenesulfonylamino)-(2-fluoro-6-chlorophenyl) chloroimine, 0.0345 g (0.171 mmol)of 4-bromo-3-methyl-2-thiophenecarbonitrile, 0.035 g (0.261 mmol) of aluminum trichloride and 1.5 mL of 1,2-dichlorobenzene was heated to 128–132° C. over one hour and held there for 1.5 hours. After cooling, the mixture was diluted with 5 mL of methylene chloride and washed with 5 mL of 2 N sodium hydroxide solution. The organic layer and one 2 mL extraction of the aqueous layer were combined, dried (sodium sulfate) and concentrated by rotatory evaporation to afford 0.067 g of an oil. This material was purified by chromatography on 11 g of silica gel (85/15, hexane-ethyl acetate, v/v) to yield 0.046 g (73%) of a colorless glass that slowly crystallized; $^1$H NMR (CDCl$_3$) 7.49 (s, 1H, thiophene-H), 7.40–7.29 (2H, m, Ph-H), 7.14–7.07 (1H, m, Ph-H), 4.00 (s, 3H, triazole-CH$_3$) and 2.35 (s, 3H, thiophene-CH$_3$); GC-MS (EI) 385/387 (M+).

EXAMPLE 5

4-Bromo-3-methyl-2-thiophenecarbonyl chloride

This example illustrates the process of Scheme III.
A. Ethyl 3-methyl-2-thiophenecarboxylate via palladium catalyzed carbonylation of 2-bromo-3-methylthiophene (Scheme III, step f)

2-Bromo-3-methylthiophene (Lancaster, 26.4 g, 0.149 mol), Pd(OAc)$_2$ (0.213 g, 0.95 mmol), 1,3-bis (diphenylphosphino) propane (0.49 g, 1.2 mmol), Na$_2$CO$_3$ (21.1 g, 0.20 mol), and 200 mL abs EtOH were placed into a 450 mL Hastalloy-C stirred pressure reactor, purged with N$_2$, then pressurized with 490 psig CO, and the stirring reactor was heated to 120° C. for 36 hrs. Analysis of the reaction mixture by gas chromatography showed 1.3% and 96.9% area % starting bromomethylthiophene and carbonylation product, respectively. After cooling and venting, the reactor contents were filtered and evaporated to give a light yellow oil/solid mixture.

This residue was extracted with 1,2-dichloroethane and water, and the organic phase was evaporated to give an oil. Filtration of this oil to remove residual salt gave 20.7 g (81% wt. % yield) of orange oil as ethyl 3-methyl-2-thiophenecarboxylate. $^{13}$C NMR {$^1$H} CDCl$_3$: δ 162.8, 145.9, 131.7, 129.9, 127.0, 60.6, 15.9, 14.4 ppm.
B. Ethyl 4-bromo-3-methyl-2-thiophenecarboxylate (Scheme III, step g)

A solution of ethyl 3-methyl-2-thiophenecarboxylate (20.0 g, 0.118 mol) and sodium hydroxide (12.3 g, 0.307 mol) in acetic acid (75 mL) was heated to 60° C. Bromine (46.9 g, 0.294 mol) was added dropwise at such a rate so as to maintain the temperature of the reaction mixture at <85° C. When the addition was complete, the resulting solution was stirred at 85° C. for 6 hours, at which time analysis by gas chromatography/mass spectrometry showed complete conversion to ethyl 4,5-dibromo-3-methyl-2-thophenecarboxylate. The solution was allowed to cool to 50° C. and zinc dust (15.4 g, 0.236 mol) was added in 3 gram portions such that the exotherm was controlled to remain below 85° C. When the addition was completed, the resulting slurry was stirred at 85° C. for one hour. The solution was filtered hot through a small bed of celite. Water (300 mL) was added and the mixture was extracted with heptanes (300 mL). The organic phase was washed with water, then concetrated to dryness to give 26.9 g (89%) as an off white oil which slowly crystallized upon standing at ambient temperature. In a similar fashion, methyl 3-methyl-2-thiophenecarboxylate may be converted methyl-4bromo-3-methyl-2-thiophenecarboxyltate in 97% yield.
C. 4-Bromo-3-methyl-2-thiophenecarboxylic acid (Scheme III, step h)

To a solution of ethyl 4-bromo-3-methyl-2-thiophenecarboxylate (5.0 g, 0.0201 mol) in THF/MeOH/ H$_2$O (4:1:1, v/v/v, 50 mL) was added NaOH (1.00 g, 0.0251 mol) and the resulting mixture was stirred at ambient temperature overnight. The mixture was acidified by adding 6 N HCl (100 mL) and water (100 mL). The resulting fine white precipitate was filtered off, washed with water and dried to give 3.80 g (86%) of 4-bromo-3-methyl-2-thiophenecarboxylic acid as a fine white solid, mp 188–189° C.
D. 4-Bromo-3-methyl-2-thiophenecarbonyl chloride (Scheme III, step i)

A slurry of 1.11 g (5 mmole) of 4-bromo-3-methyl-2-thiophenecarboxylic acid, 0.44 mL (6 mmole) of thionyl chloride, 5 drops of DMF, and 10 mL of 1,2-dichloroethane was heated at 800° C. for 1.5 h. The clear solution was cooled and concentrated on a roto-evaporator. The residue was dissolved in 5 mL of 1,2-dichloroethane and reconcentrated on a roto-evaporator to give 1.2 g of a tan solid, 97% pure (GC area). This acid chloride was used without further purification.

EXAMPLE 6

Methyl 3-methyl-thiophenecarboxylate via Gringnard reaction of 2-bromo-3-methylthiophene 2-Bromo-3-methylthiophene (10.0 g, 0.0565 mol) was slowly added dropwise over a 60 minute period to a slurry of magnesium turnings (1.72 g, 0.0706) in THF. During the course of the addition, the exotherm was controlled to <40° C. by external cooling with a water bath. After the addition was completed, the resulting mixture was stirred at ambient temperature for 60 minutes. Dimethylcarbonate (7.63 g, 0.0847 mol) was then added dropwise over a 5-minute period, and the reaction mixture was stirred at ambient temperature for 4 hours. The reaction mixture was quenched by the addition of 6 M HCl (50 mL), and extracted with ethylacetate (100 mL). The organic phase was washed with water (25 mL), followed by saturated aqueous $NaHCO_3$. Concentration of the organic phase then gave 7.38 g (84%) of methyl 3-methyl-2-thiophenecarboxylate as a light yellow oil.

EXAMPLE 7

3-(2-Chloro-6-fluorophenyl)-1-methyl-5-(4-bromo-3-methyl-2-thienyl)-1H-1,2,4-triazole This example illustrates the process of Scheme II.

A. Methyl 2-chloro-6-fluoro-N-[(4-bromo-3-methyl-2-thiophene)carbonyl]benzenecarboximidothioate (Scheme II, step c)

A mixture of 0.95 g (5 mmole) of 2-chloro-6-fluorobenzenecarbothioamide, 0.5 mL (5.5 mmole) of dimethyl sulfate, and 10 mL of 1,4-dioxane was heated at 80° C. for 1 h. The clear solution was allowed to cool to room temperature, where a white precipitate formed. To the slurry was added 1.0 mL (12.5 mmole) of pyridine, followed by 1.2 g (5 mmole) of 4-bromo-3-methyl-2-thiophenecarbonyl chloride. The reaction mixture turned brown in color and a gummy insoluble material formed which made stirring difficult. The mixture was heated at 50° C. for 1.5 h. The mixture was poured onto ice and a gummy solid formed which solidified upon stirring. Stirring was continued for 1 h, and the mixture was filtered to give 1.74 g (85% wt) of a tan powder, mp 106°–109°. This material was used without further purification.

B. 3-(2-Chloro-6-fluorophenyl)-1-methyl-5-(4-bromo-3-methyl-2-thienyl)-1H-1,2,4-triazole (Scheme II, step d)

A mixture of 1.22 g (3 mmole) of methyl 2-chloro-6-fluoro-N-[(4-bromo-3-methyl-2-thiophene)carbonyl]-benzenecarboximidothioate in 5 mL of 1,4-dioxane was heated to 75° C. To the solution was added in one portion 0.24 mL (4.5 mmole) of methylhydrazine in 0.5 mL of water. After heating here for 1.5 h, the solution was cooled and poured onto ice. The initially formed gummy solid was stirred for 1 h and filtered to give 1.03 g (89% wt) of an off-white powder. GC analysis indicated 96.4/1.7 area ratio of the desired product to off-isomer.

EXAMPLE 8

3-(2-Chloro-6-fluorophenyl)-1-methyl-5-(4-bromo-3-methyl-2-thienyl)-1H-1,2,4-triazole Into 250-mL three-necked round bottom flask equipped with a mechanical stirrer and condenser under an atmosphere of nitrogen was added 19.26 g of 3-(2-chloro-6-fluorophenyl)-1-methyl-5-(4,5-dibromo-3-methyl-2-thienyl)-1H-1,2,4-triazole, 72 mL of acetic acid, 16 mL of water, and 3.25 g of zinc dust. The temperature of the reaction mixture was heated to 100° C. and was maintained at that temperature. After three hours the mixture was allowed to cool to room temperature and was poured into ether (500 mL) and washed with water (2×150 mL), saturated sodium bicarbonate (3×150 mL), brine, dried ($Na_2SO_4$) and the solvent removed in vacuo to give 15.4 g (96.4% yield) of the title compound as a white solid: mp 120–121° C; $^1$H NMR ($CDCl_3$) δ 7.5 (s, b, 1H), 7.3–7.4 (m, 2H), 7.1 (m, 1H), 4.0 (s, 3H), 2.35 (s, 3H).

The following table identifies the compounds that were made and summarizes the biological test data collected for them:

TABLE

| Cmpd No | $R^1$ | $R^2$ | $R^3$ | $R^4$ | mp ° C. | $Ca^\dagger$ | $TSSM^\ddagger$ | $WF^*$ |
|---|---|---|---|---|---|---|---|---|
| 1 | F | Cl | $CH_3$ | Br | 111–112 | A | A | A |
| 2 | F | Cl | $CH_3$ | Cl | 117–118 | B | A | A |
| 3 | F | Cl | Br | Br | 126–128 | A |   | A |

$CA^\dagger$ refers to activity at 50 ppm against cotton aphid,
$TSSM^\ddagger$ refers to activity at 100 ppm against two-spotted spider mite, and
$WF^*$ refers to activity at 200 ppm against whitefly.

$CA^\dagger$ refers to activity at 50 ppm against cotton aphid, $TSSM^\ddagger$ refers to activity at 100 ppm against two-spotted spider mite, and $WF^*$ refers to activity at 200 ppm against whitefly.

In each case the rating scale is as follows

| % Control | Rating |
|---|---|
| 91–100 | A |
| 81–90 | B |
| 71–80 | C |
| 61–70 | D |
| 51–60 | E |
| less than 51 | F |
| inactive | G |

Insecticide and Miticide Utility

The compounds of the invention are also useful for the control of insects (including whitefly), mites, and aphids. Therefore, the present invention also is directed to a method for inhibiting an insect, mite, or aphid which comprises applying to a locus of the insect or mite an insect- or mite-inhibiting amount of a compound of formula (1).

The compounds are useful for reducing populations of insects and mites and are useful in a method of inhibiting an insect or mite population which comprises applying to a locus of the insect or mite an effective insect- or mite-inactivating amount of a compound of formula (1). The "locus" of insects or mites is a term used herein to refer to the environment in which the insects or mites live or where their eggs are present, including the air surrounding them, the food they eat, or objects which they contact. For example, plant-ingesting insects or mites can be controlled by applying the active compound to plant parts that the insects or mites eat, particularly the foliage. It is contemplated that the compounds might also be useful to protect textiles, paper, stored grain, or seeds by applying an active compound to such substance. The term "inhibiting an insect or mite" refers to a decrease in the numbers of living insects or mites, or a decrease in the number of viable insect or mite eggs. The extent of reduction accomplished by a compound depends, of course, upon the application rate of the compound, the particular compound used, and the target insect or mite species. At least an inactivating amount should be used. The terms "insect- inactivating amount" and "mite-inactivating amount" are used to describe the amount, which is sufficient to cause a measurable reduction in the treated insect or mite, population. Generally an amount in the range from about 1 to about 1000 ppm active compound is used.

In a preferred embodiment, the present invention is directed to a method for inhibiting a mite or aphid which comprises applying to a plant an effective mite- or aphid-inactivating amount of a compound of formula (1).

Insecticidal Test for Cotton Aphid (*Aphis gossypii*):

To prepare spray solutions, 1 mg of each test compound was dissolved into 2 mL of a 90:10 acetone:ethanol solvent. This 1 mL of chemical solution was added to 19 mL of water containing 0.05% Tween 20 surfactant to produce a 50 ppm spray solution.

Squash cotyledons were infested with cotton aphid (all life stages) 16–20 hours prior to application of spray solution. The solution was sprayed on both sides of each infested squash cotyledon (0.5 mL×2 each side) with a sweeping action until runoff. The plants were allowed to air dry and held for 3 days in a controlled room at 26° C. and 40% RH after which time the test was graded. Grading was by actual count using a dissecting microscope and comparison of test counts to the untreated check. Results are given in Table 1 as percent control based on population reduction versus the untreated.

Insecticidal Test for Two-spotted Spider Mite (*Tetranychus urticae*)

Ovicide Method:

Ten adult female two-spotted spider mites were placed on eight 2.2 cm leaf discs of cotton leaf, allowed to oviposit over 24 hours, and thereafter removed. The leaf discs were sprayed with 100 ppm test solutions using a hand syringe, then allowed to dry with sixteen discs left untreated as a negative control. Discs were placed on an agar substrate and held at 24° C. and 90% relative humidity for 6 days. Percent control based on the number of hatched larvae on treated discs and the number on untreated discs is reported in Table 1.

Evaluation of Tests Compounds on Sweetpotato Whitefly (*Bemisia tabacia*) Under Laboratory Conditions Four mg of each test compound was dissolved by adding 4 ml of a 90:10 acetone:ethanol solvent mixture to the vial containing the sample compound. This solution was added to 16 ml of water containing 0.05% Tween 20 surfactant to produce 20 ml of an 200 ppm spray solution.

Five-week-old cotton plants reared in a greenhouse were stripped of all foliage except for the two uppermost true leaves that were greater than 5 cm in diameter. These plants were then placed into a laboratory colony of whiteflies for two days for oviposition by the colony females. All whiteflies were then removed from the test plants with pressurized air. The spray solution was then applied to the test plants with a hand-held syringe fitted with hollow cone nozzle. One mL spray solution was applied to each leaf top and bottom for a total of 4 mL per plant. Four replications of each test compound utilized a total of 16 mL spray solution. Plants were air dried and then placed in a holding chamber (28° C. and 60% RH) for 13 days. Compound efficacy was evaluated by counting, under an illuminated magnifying glass, the number of large nymphs (3rd–4th instar) per leaf. Percent control based on reduction of large nymphs of a test compound compared to solution-only (no test compound) sprayed plants is reported in Table 1.

Compounds of the invention have been tested on and shown activity against, for example, the following specific pests: California Red Scale, Citrus Flat Mite, Green Peach Aphid, Green Rice Leafhopper (foliar spray), Brown Planthopper (foliar spray), Green Rice Leafhopper (systemic), Brown Planthopper (systemic), Citrus Rust Mite, Citrus Red Mite, European Red Mite, Pacific Spider Mite, Two spotted spider mite, Yellow Spider Mite, Citrus Flat Mite, Cereal aphid, Cotton aphid, Apple aphid, Cabbage aphid, and Green Peach aphid.

In addition to being effective against mites, aphids, and insects when applied to foliage, compounds of formula (1) have systemic activity. Accordingly, another aspect of the invention is a method of protecting a plant from insects which comprises treating plant seed prior to planting it, treating soil where plant seed is to be planted, or treating soil at the roots of a plant after it is planted, with an effective amount of a compound of formula (1).

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects, mites, and aphids is not critical and can readily be determined by those skilled in the art in view of the examples above. In general, concentrations of from-10 ppm to 5000 ppm of compound are expected to provide good control. With many of the compounds, concentrations of from 100 to 1500 ppm will suffice. For field crops, such as soybeans and cotton, a suitable application rate for the compounds is about 0.5 to 1.5 lb/A, typically applied in 5–20 gal/A of spray formulation containing 1200 to 3600 ppm of compound. For citrus crops, a suitable application rate is from about 100 to 1500 gal/A spray formulation, which is a rate of 100 to 1000 ppm.

The locus to which a compound is applied can be any locus inhabited by an insect or arachnid, for example, vegetable crops, fruit and nut trees, grape vines, and ornamental plants. Inasmuch as many mite species are specific to a particular host, the foregoing list of mite species provides exemplification of the wide range of settings in which the present compounds can be used.

Because of the unique ability of mite eggs to resist toxicant action, repeated applications may be desirable to control newly emerged larvae, as is true of other known acaricides.

The following formulations of compounds of the invention are typical of compositions useful in the practice of the present invention.

| A. 0.75 Emulsifiable Concentrate | |
| --- | --- |
| Compound of formula (1) | 9.38% |
| "TOXIMUL D" (nonionic/anionic surfactant blend) | 2.50% |
| "TOXIMUL H" (nonionic/anionic surfactant blend) | 2.50% |
| "EXXON 200" (naphthalenic solvent) | 85.62% |

| B. 1.5 Emulsifiable Concentrate | |
| --- | --- |
| Compound of formula (1) | 18.50% |
| "TOXIMUL D" | 2.50% |
| "TOXIMUL H" | 2.50% |
| "EXXON 200" | 76.50% |

| C. 1.0 Emulsifiable Concentrate | |
| --- | --- |
| Compound of formula (1) | 12.5% |
| N-methylpyrrolidone | 25.00% |
| "TOXIMUL D" | 2.50% |
| "TOXIMUL H" | 2.50% |
| "EXXON 200" | 76.50% |

| D. 1.0 Aqueous Suspension | |
| --- | --- |
| Compound of formula (1) | 12.00% |
| "PLURONIC P-103" (block copolymer of propylene oxide and ethylene oxide, surfactant) | 1.50% |
| "PROXEL GXL" (preservative) | .05% |
| "AF-100" (silicon based antifoam agent) | .20% |
| "REAX 88B" (lignosulfonate dispersing agent) | 1.00% |
| propylene glycol | 10.00% |
| veegum | .75% |
| xanthan | .25% |
| water | 74.25% |

| E. 1.0 Aqueous Suspension | |
| --- | --- |
| Compound of formula (1) | 12.50% |
| "MAKON 10" (10 moles ethyleneoxide nonylphenol surfactant) | 1.00% |
| "ZEOSYL 200" (silica) | 1.00% |
| "AF-100" | 0.20% |
| "AGRIWET FR" (surfactant) | 3.00% |

-continued

| E. 1.0 Aqueous Suspension | |
|---|---|
| 2% xanthan hydrate | 10.00% |
| water | 72.30% |

| F. 1.0 Aqueous Suspension | |
|---|---|
| Compound of formula (1) | 12.50% |
| "MAKON 10" | 1.50% |
| "ZEOSYL 200" (silica) | 1.00% |
| "AF-100" | 0.20% |
| "POLYFON H" (lignosulfonate dispersing agent) | 0.20% |
| 2% xanthan hydrate | 10.00% |
| water | 74.60% |

| G. Wettable Powder | |
|---|---|
| Compound of formula (1) | 25.80% |
| "POLYFON H" | 3.50% |
| "SELLOGEN HR" | 5.00% |
| "STEPANOL ME DRY" | 1.00% |
| gum arabic | 0.50% |
| "HISIL 233" | 2.50% |
| Barden clay | 61.70% |

| H. 1.0 Aqueous Suspension | |
|---|---|
| Compound of formula (1) | 12.40% |
| "TERGITOL 158-7" | 5.00% |
| "ZEOSYL 200" | 1.0% |
| "AF-1G0" | 0.20% |
| "POLYFON H" | 0.50% |
| 2% xanthan solution | 10.00% |
| tap water | 70.90% |

| I. 1.0 Emulsifiable Concentrate | |
|---|---|
| Compound of formula (1) | 12.40% |
| "TOXIMUL D" | 2.50% |
| "TOXIMUL H" | 2.50% |
| "EXXON 200" | 82.60% |

| J. Wettable Powder | |
|---|---|
| Compound of formula (1) | 25.80% |
| "SELLOGEN HR" | 5.00% |
| "POLYFON H" | 4.00% |
| "STEPANOL ME DRY" | 2.00% |
| "HISIL 233" | 3.00% |
| Barden clay | 60.20% |

| K. 0.5 Emulsifiable Concentrate | |
|---|---|
| Compound of formula (1) | 6.19% |
| "TOXIMUL H" | 3.60% |
| "TOXIMUL D" | 0.40% |
| "EXXON 200" | 89.81% |

| L. Emulsifiable Concentrate | |
|---|---|
| Compound of formula (1) | 5 to 48 |
| surfactant or surfactant blend | 2 to 20% |
| Aromatic Solvent or Mixture | 55 to 75% |

We claim:

1. A compound of the formula (1)

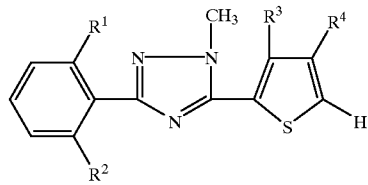

wherein $R^1$ and $R^2$ are independently F or Cl; and a) $R^3$ is $CH_3$ and $R^4$ is Cl or Br, or b) $R^3$ and $R^4$ are both Br.

2. The compound of claim 1 that is 3-(2-chloro-6-fluorophenyl)-5-(3-methyl-4-bromothien-2-yl)-1-methyl-1H-[1,2,4]-triazole.

3. The compound of claim 1 that is 3-(2-chloro-6-fluorophenyl)-5-(3-methyl-4-chlorothien-2-yl)-1-methyl-1H-[1,2,4]-triazole.

4. The compound of claim 1 that is 3-(2-chloro-6-fluorophenyl)-5-(3,4-dibromothien-2-yl)-1-methyl-1H-[1,2,4]-triazole.

5. A composition for controlling insects or mites which comprises a compound of claim 1 in combination with a phytologically-acceptable carrier.

6. A method of controlling insects or mites which comprises applying to a locus where control is desired an insect- or mite-inactivating amount of a compound of claim 1.

7. A method of controlling whitefly which comprises applying to a locus where control is desired a whitefly inactivating amount of a compound of claim 1.

8. A method of controlling mites which comprises applying to a locus where control is desired a mite-inactivating amount of a compound of claim 1.

9. A method of controlling aphids which comprises applying to a locus where control is desired an aphid inactivating amount of a compound of claim 1.

10. A method of protecting a plant from aphids, mites, or insects which comprises treating plant seed prior to planting it, treating soil where plant seed is to be planted, or treating soil at the roots of a plant after it is planted, with an effective amount of a compound of claim 1.

* * * * *